United States Patent [19]

Lake

[11] 4,097,542

[45] Jun. 27, 1978

[54] PRODUCTION OF ALKYLBENZENES

[75] Inventor: Ivan James Samuel Lake, Middlesbrough, England

[73] Assignee: Imperial Chemical Industries Limited, London, England

[21] Appl. No.: 827,098

[22] Filed: Aug. 23, 1977

[30] Foreign Application Priority Data

Sep. 29, 1976 United Kingdom ............... 40388/76

[51] Int. Cl.$^2$ ............................................... C07C 3/52
[52] U.S. Cl. ........................... 260/671 M; 260/671 C; 260/671 R
[58] Field of Search ........... 260/671 M, 671 R, 671 C

[56] References Cited

U.S. PATENT DOCUMENTS

| | | | |
|---|---|---|---|
| 3,965,208 | 6/1976 | Butter et al. | 260/671 C |
| 4,002,698 | 1/1977 | Kaeding | 260/671 C |
| 4,060,590 | 11/1977 | Whittam et al. | 423/328 |

*Primary Examiner*—Delbert E. Gantz
*Assistant Examiner*—C. E. Spresser
*Attorney, Agent, or Firm*—Cushman, Darby & Cushman

[57] ABSTRACT

Aromatic hydrocarbons are alkylated in the presence of zeolite nu-1 as catalyst. The invention particularly relates to the production of xylene by the methylation of toluene at temperatures in the range 300° to 600° C, preferably in the range from about 450° to 550° C.

11 Claims, No Drawings

PRODUCTION OF ALKYLBENZENES

This invention relates to the production of alkylbenzenes by the alkylation of aromatic hdyrocarbons.

Large quantities of alkylbenzenes, especially toluene and xylenes, are now manufactured throughout the world. The processes used frequently involve the reforming of a naphtha feedstock and one of the problems asssociated with these reforming processes has been the need to obtain the most useful product spectrum, i.e. the most useful quantitative distribution of the various aromatic hydrocarbon compounds in the product. For example, benzene and xylenes are of far greater commercial value than toluene and $C_9$ and higher aromatic hydrocarbons. Thus it is now not unusual in aromatic hydrocarbon production plants to provide for at least some of the toluene and/or the $C_9$ or $C_{9+}$ aromatic hydrocarbons which are produced to be converted to benzenes and xylenes, for example by dealkylation to benzene and/or disproportionation to benzene and xylenes. Alternatively, an aromatic hydrocarbon may be alkylated with a suitable alkylating agent, for example toluene may be converted to a mixture of xylenes.

According to the present invention a process for effecting the alkylation of aromatic hydrocarbons comprises contacting an aromatic hydrocarbon with an alkylating agent under reaction conditions which are effective for accomplishing alkylation of the aromatic hydrocarbon and in the presence of a catalyst comprising zeolite nu-1 as hereinafter defined.

The catalyst used in the process of this invention comprises the zeolite designated "nu-1" which is more particularly described in U.S. Pat. No. 4,060,590, the disclosure of which is incorporated herein by reference. Zeolite nu-1 has a composition (in terms of mole ratios) in the range 0.9 to 1.3 $R_2O:Al_2O_3$ : 20 to 150$SiO_2$ : 0 to 40$H_2O$ where R is one or more of hydrogen, ammonium, phosphonium or 1/n of a cation of a metal of valency $n$ and having an X-ray diffraction pattern when R is H substantially as shown in Table 1.

TABLE 1
ZEOLITE nu-1 IN HYDROGEN FORM

| d(A) | 100 I/Io | d(A) | 100 I/Io |
|------|----------|------|----------|
| 8.87 | 18 | 3.965 | 73 |
| 8.28 | 69 | 3.845 | 74 |
| 6.53 | 43 | 3.81 | 22 |
| 6.19 | 75 | 3.687 | 16 |
| 4.43 | 52 | 3.508 | 29 |
| 4.30 | 51 | 3.256 | 27 |
| 4.08 | 37 | 2.858 | 15 |
| 4.03 | 100 | | |

This definition includes both freshly prepared, i.e. untreated, zeolite nu-1 and also forms of it resulting from dehydration and/or calcination and/or ion exchange. In freshly prepared nu-1 zeolite, R is or includes ammonium or phosphonium selected from methylated quaternary ammonium and methylated quaternary phosphonium and carionic degradation products thereof (referred to hereinafter as Q) and may include an alkali-metal, especially sodium. The freshly-prepared material may also contain loosely-bound occluded quaternary compound but this does not constitute part of the composition for the definition. The proportion of such compound is typically 0.5 to 1.5 mole of $Q_2O$ per mole of $Al_2O_3$.

The date shown in Table 1 include estimated measurement errors and represent ranges of variation such as are common in the zeolite art as a result of impurities, of changes in the associated cations represented by R, and variations in detailed crystal structure within the scope of the essential nu-1 structure. In particular, the d-spacing in Table 1 may be up to 4% larger or 2% smaller, the zeolite may contain a combination of nu-1 forms from various parts of the d-spacing range, and the 6.5 to 6.6A line may be split into two.

Zeolite nu-1 may be made by reacting an aqueous mixture comprising at least one silica source, at least one alumina source, and at least one methylated quaternary ammonium or methylated quaternary phosphonium compound, the mixture having the molar composition:

$SiO_2/Al_2O_3$ : at least 10, preferably 20 to 200, especially 40 to 100.

$Na_2O/SiO_2$ : 0 to 0.4, especially 0.05 to 0.25

$(Na_2O + Q_2O)/SiO_2$ : 0.1 to 6.0, preferably 0.1 to 5.0, especially 0.2 to 0.3.

$H_2O/(Na_2O + Q_2O)$ : 5 to 500, especially 100 to 300

$Q_2O/(Na_2 + Q_2O)$ : 0.05 to 1.0, especially 0.4 to 0.7.

where Q is methylated quaternary ammonium or methylated quaternary phosphonium. $Na_2O$ and $Q_2O$ refer to free $Na_2O$ and $Q_2O$ only.

The expressions "free $Na_2O$" and "free $Q_2O$" are generally understood in the zeolites art to denote hydroxides or salts of very weak acids such as aluminic or silicic acid such that such $Na_2O$ and $Q_2O$ are effective in the zeolite synthesis reaction.

In general, the cation(s) of zeolite nu-1 can be replaced by any cation(s) of metals and particularly by those in Groups IA, IB, IIA, IIB, III (including rare earths), VIIA (including manganese), VIII (including noble metals) of the Periodic Table, and by lead and bismuth.

In order to prepare a catalyst, zeolite nu-1 can be incorporated in an inorganic matrix with other materials which can be either inert or catalytically active. The matrix may be present simply as a binding agent to hold the small zeolite particles together, or it may be added as a diluent to control the amount of conversion in a process which may otherwise proceed at too high a rate, leading to catalyst fouling as a result of excessive coke formation. Typical inorganic diluents include kaolinic clays, bentonites, montmorillonites, sepiolite, attapulgite, Fuller's earth, synthetic porous materials such as $SiO_2 - Al_2O_3$, $SiO_2 - ZrO_2$, $SiO_2 - ThO_2$, $SiO_2 - BeO$, $SiO_2 - TiO_2$ and any combination of these oxides. The relative proportions of nu-1 and binder may vary from 1:9 by weight of the composition.

Examples of the hydrocarbons which may be alkylated using the process of this invention include, for example, toluene.

The preferred alkylating agents for use in the process of this invention are any one or more of alcohols, for example methanol, alkylesters for example methyl esters, alkyl ethers, for example dimethylether and alkyl halides.

Suitably, the molar ratio of aromatic hydrocarbon to alkylating agent is in the range 0.1 : 1 to 10:1, more preferably in the range 0.2 : 1 to 5:1.

Preferred operating conditions for the process of this invention include a temperature in the range 300° to 600° C, more preferably in the range 400° to 500° C, a reaction pressure in the range 1 to 100 Bar, more preferably in the range 1 to 60 Bar, and a weight hourly space velocity (weight of feed per unit weight of catalyst per hour) in the range 0.05 to 10, more preferably in the range 0.1 to 5. In general, higher space velocities are used at higher reaction temperatures.

Optionally, the process of this invention is effected in the presence of hydrogen. Suitable mole ratios of hydrogen to the aromatic hydrocarbon lie in the range 0.1:1 to 20:1, more preferably in the range 1:1 to 10:1.

The process of the present invention is particularly applicable to the methylation of toluene to xylenes. Suitable methylating agents include methanol and dimethylether. It appears that at relatively low toluene conversions, say of about 15% or less, some control can be exercised over the selectivity of the reaction in forming the various xylene isomers. At reaction temperatures up to about 350° C, ortho-xylene is the major product whereas at reaction temperatures in the range of about 450° to about 550° C, para-xylene becomes the major product. At relatively high toluene conversions and particularly at the higher temperatures, xylenes are obtained in approximate equilibrium.

EXAMPLE

A quantity of zeolite nu-1 in the hydrogen form was prepared as described in U.S. Pat. No. 4,060,590. A reaction mixture having the composition 2.5 Na$_2$O : 16.2 TMA.OH:Al$_2$O$_3$ : 88SiO$_2$ : 2468H$_2$O, where TMA is tetramethylammonium, was prepared by dissolving 3.20 g. of sodium hydroxide pellets, 3.33g of sodium aluminate and 118g of tetramethylammonium hydroxide (25% solution) in 800 ml. of water. This solution was then stirred into 85.0 g. of fine silica and 21.0g. of a second form of fine silica which had been pre-calcined. Stirring was continued until the mixture was a smooth creamy consistency.

The mixture was then reacted in a stainless steel autoclave at 176° C for 6 days. The solid product was collected in a filter and dried at 200° C for 2 hours. The zeolite obtained was identified as "nu-1" by X-ray diffraction.

The zeolite was ion-exchanged by heating 20g. batches at 50° C for 1 hour, with stirring, with 300 ml of an aqueous ammonium chloride solution (67g. ammonium chloride/liter). This procedure was repeated twice more for each batch. The product was filtered and dried at 200° C overnight. The ion-exchanged zeolite thus obtained contained 0.17% sodium and 0.95% aluminium and it was then mixed with 50% of its weight of a high surface-area alumina. The mixture was formed into 3mm pellets and calcined at 550° C in air.

A mixture containing equal moles of toluene and methanol was passed over 3.0 g. of the catalyst pellets in a glass tubular reactor at a rate of 4.7g. mixture per hour. The reaction temperature was 450° and the pressure was atmospheric. After 6 hours the composition of the aromatics in the reaction product was as follows, (% by weight):

| Compound | % by weight |
|---|---|
| Benzene | 0.06 |
| Toluene | 74.4 |

-continued

| Compound | % by weight |
|---|---|
| Para-xylene | 10.7 |
| Meta-xylene | 5.8 |
| Ortho-xylene | 4.9 |
| Ethylbenzene | 0.03 |
| C$_9$ aromatics | 4.0 |
| C$_{10}$+ aromatics | 0.04 |

Para-xylene thus represents 50% of the C$_8$ aromatic fraction in the product.

I claim:

1. A process for effecting the alkylation of an aromatic hydrocarbon which comprises contacting an aromatic hydrocarbon with an alkylating agent under reaction conditions which are effective for accomplishing alkylation of the aromatic hydrocarbon and in the presence of a catalyst comprising zeolite nu-1 having a composition expressed by the formula

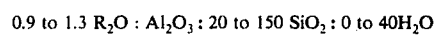

0.9 to 1.3 R$_2$O : Al$_2$O$_3$ : 20 to 150 SiO$_2$ : 0 to 40H$_2$O where R is one or more of hydrogen, ammonium, phosphonium of 1/n of a cation having a valency $n$ and having an X-ray diffraction pattern when R is H substantially as shown in Table 1.

2. A process as claimed in claim 1 in which the aromatic hydrocarbon is toluene.

3. A process as claimed in claim 1 in which the alkylating agent is selected from the group consisting of alcohols, alkyl esters, alkyl ethers and alkyl halides.

4. A process as claimed in claim 3 in which the alkylating agent is methanol.

5. A process as claimed in claim 1 in which the molar ratio of aromatic hydrocarbon to alkylating agent is in the range 0.1:1 to 10:1.

6. A process as claimed in claim 1 in which the process is operated at a reaction temperature which lies in the range 300° to 600° C, a reaction pressure which lies in the range 1 to 100 Bar and a weight hourly space velocity which lies in the range 0.05 to 10.

7. A process as claimed in claim 1 in which the process is operated in the presence of hydrogen.

8. A process as claimed in claim 7 in which the mole ratio of hydrogen to the aromatic hydrocarbon lies in the range 0.01 to 1 to 20 : 1.

9. A process as claimed in claim 1 for the production of xylene which comprises reacting toluene with a methylating agent at a toluene conversion which is not greater than 15% and at a temperature not greater than 350° C.

10. A process as claimed in claim 1 for the production of xylene which comprises reacting toluene with a methylating agent at a toluene conversion which is not greater than 15% and at a temperature which is in the range of about 450° to about 550° C.

11. A process as claimed in claim 1 for the production of xylene which comprises reacting toluene with methanol at a temperature in the range of 400° to 500° C, at a pressure in the range 1 to 60 Bar, at a molar ratio of toluene to methanol which is in the range 0.2 : 1 to 5:1, at a toluene conversion not greater than 15% and in the presence of zeolite nu-1 in the hydrogen form.

* * * * *